(12) United States Patent
Schneider et al.

(10) Patent No.: US 9,244,054 B2
(45) Date of Patent: Jan. 26, 2016

(54) SYSTEMS AND METHODS FOR DETERMINING A STATE OF DETERIORATION OF ENGINE OIL USING MULTIPLE PRESELECTED OIL PROPERTIES

(75) Inventors: Eric W. Schneider, Shelby Township, MI (US); Spyros Tseregounis, Davis, CA (US); Matthew J. Snider, Howell, MI (US); Michael Seemann, Bischofsheim (DE)

(73) Assignee: GM Global Technology Operations LLC, Detroit, MI (US)

( * ) Notice: Subject to any disclaimer, the term of this patent is extended or adjusted under 35 U.S.C. 154(b) by 761 days.

(21) Appl. No.: 13/545,368

(22) Filed: Jul. 10, 2012

(65) Prior Publication Data

US 2014/0019068 A1    Jan. 16, 2014

(51) Int. Cl.
| | | |
|---|---|---|
| *G06F 19/00* | (2011.01) | |
| *G01N 33/22* | (2006.01) | |
| *G01N 33/28* | (2006.01) | |
| *F01M 11/10* | (2006.01) | |
| *G01N 21/3577* | (2014.01) | |
| *G01N 11/00* | (2006.01) | |

(52) U.S. Cl.
CPC ............ *G01N 33/2888* (2013.01); *G06F 19/00* (2013.01); *F01M 11/10* (2013.01); *F01M 2011/14* (2013.01); *G01N 11/00* (2013.01); *G01N 21/3577* (2013.01)

(58) Field of Classification Search
CPC .............. G01N 33/2888; G01N 11/00; G01N 2011/0093; G01M 15/042; G07C 5/006; F01M 11/10; F01M 2011/1486; F01M 2011/14; F01M 11/12; F01M 2011/1473; F01M 2011/148; F01M 1/16; F01M 2011/142; F01M 2011/1453; F01M 2011/0029; F01M 2011/1413; F01M 2011/1426; F01M 2011/146
USPC ..................... 73/114.55, 53.05, 53.07, 61.44; 340/457.4, 603, 439, 450, 450.3; 701/29.5, 29.1
See application file for complete search history.

(56) References Cited

U.S. PATENT DOCUMENTS

| | | | |
|---|---|---|---|
| 8,087,287 B2 * | 1/2012 | Cummings ................. 73/53.05 |
| 2008/0027661 A1 * | 1/2008 | Aikawa .......................... 702/50 |
| 2010/0242449 A1 * | 9/2010 | Paterson ........................ 60/286 |
| 2010/0299080 A1 * | 11/2010 | Willmann et al. .............. 702/25 |

* cited by examiner

Primary Examiner — Mischita Henson
Assistant Examiner — Christine Liao
(74) Attorney, Agent, or Firm — Mickki D. Murray, Esq.; Parks Wood LLC

(57) ABSTRACT

Systems and methods for automatically evaluating the useful life of an engine oil based on data corresponding to a plurality of preselected key oil properties. The evaluation includes determining, in connection with each of the pre-selected key oil properties, a first current measured oil property value, a first reference oil property value, a first deterioration-limit value, and a first weighting factor. The evaluation also includes determining a single index value, indicating a state of deterioration of the engine oil, in a calculation using each of the values and factors.

20 Claims, 3 Drawing Sheets

SYSTEMS AND METHODS FOR DETERMINING A STATE OF DETERIORATION OF ENGINE OIL USING MULTIPLE PRESELECTED OIL PROPERTIES

TECHNICAL FIELD

The present disclosure relates generally to systems and methods for determining a state of deterioration of engine oil and, more particularly, to systems and methods for determining an objective index value indicative of deterioration of engine oil, for spark-ignited engines, based on multiple preselected oil properties.

BACKGROUND

Engine oil deteriorates in various ways as it is used in an engine over time. Degradation sources include thermal stresses, tribological interactions (or the interaction of adjacent surfaces under relative motion), and byproducts of combustion. Evaluators of engine oil degradation have, heretofore, considered various key oil properties separately, if at all.

While one evaluator may measure only viscosity of an oil sample, for instance, and conclude based solely on that measurement whether the oil has useful life remaining, another may, measure only a total acid number (or TAN; the amount of potassium hydroxide in milligrams that is needed to neutralize the acids in one gram of oil), and base their conclusion solely on that measurement.

Determinations about overall oil quality based on only one parameter (e.g., viscosity or TAN) have inherent shortcomings because oil deteriorates in many distinct ways. Although an oil sample may have an undesirably high TAN, for example, the oil can be satisfactory overall for continued use. And while a sample may have a healthy viscosity, the oil can be unsatisfactory overall for continued use.

There is a need for technology that automatically generates an objective indication of oil quality and remaining oil life, if any, based on multiple preselected key oil properties taken together.

SUMMARY

The present disclosure in one aspect relates to a system for automatically evaluating the degree of deterioration of an engine oil based on data corresponding to a plurality of preselected key oil properties. The evaluation includes determining, in connection with each of the pre-selected key oil properties, a first current measured oil property value, a first reference oil property value, a first deterioration-limit value, and a first weighting factor. The evaluation also includes determining a single index value, indicating a state of deterioration of the engine oil, in a calculation using each of the values and factors.

In another aspect, the present disclosure relates to a method, performed by a computer processer executing computer-executable code, or instructions, stored at a non-transitory computer readable storage medium. The method includes performance of the evaluation acts described in the preceding paragraph.

In still another aspect, the present disclosure relates to a non-transitory computer-readable storage medium like that described in the preceding paragraph.

Other aspects of the present invention will be in part apparent and in part pointed out hereinafter.

DETAILED DESCRIPTION

Figure 1:
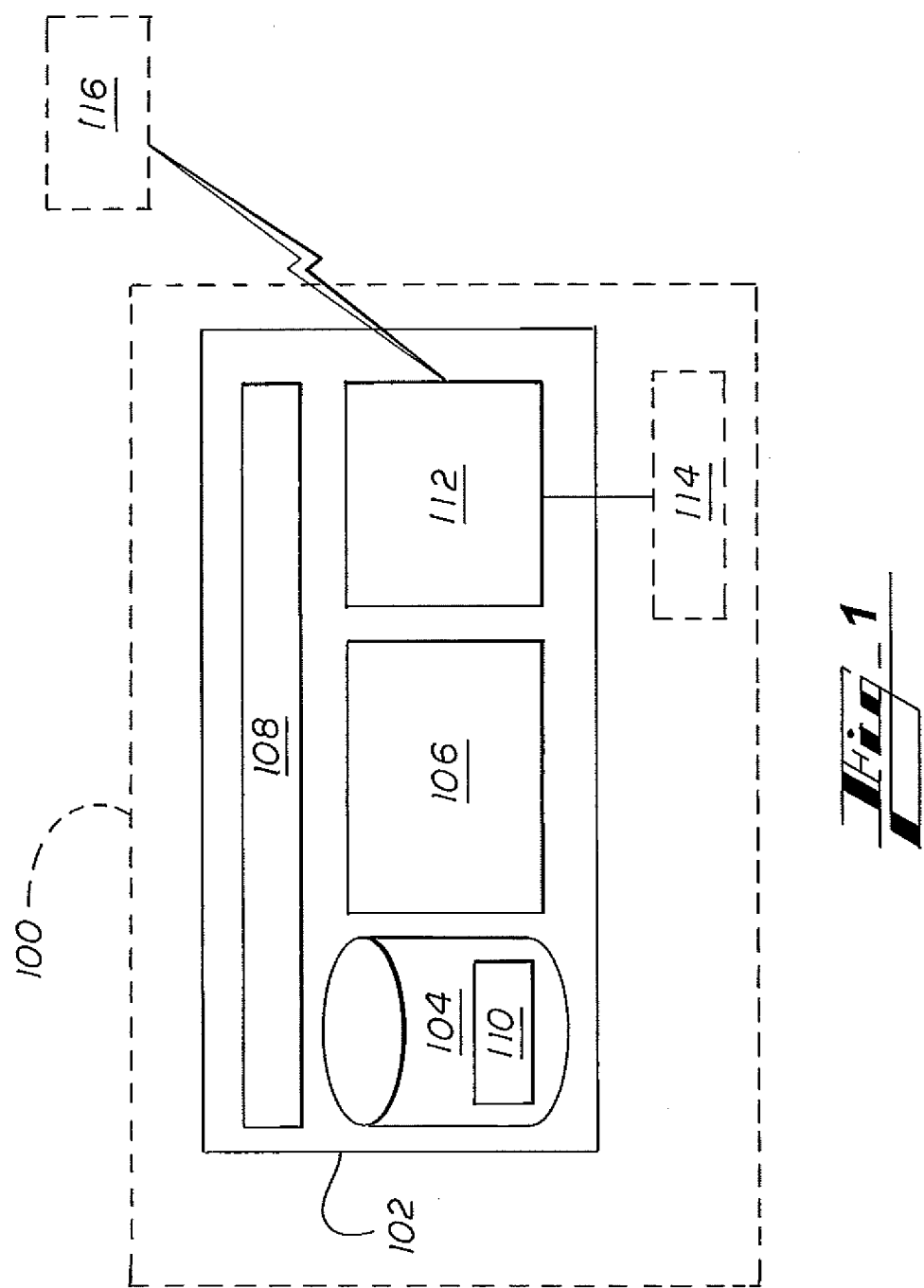
FIG. 1 illustrates a schematic block diagram of a system for implementing the present technology according to an embodiment of the present disclosure.

As required, detailed embodiments of the present technology are disclosed herein. The disclosed embodiments are merely examples that may be embodied in various and alternative forms, and combinations thereof. As used herein, for example, "exemplary," and similar terms, refer expansively to embodiments that serve as an illustration, specimen, model or pattern.

The figures are not necessarily to scale and some features may be exaggerated or minimized, such as to show details of particular components. In some instances, well-known components, systems, materials or methods have not been described in detail in order to avoid obscuring the present disclosure. Therefore, specific structural and functional details disclosed herein are not to be interpreted as limiting, but merely as a basis for the claims and as a representative basis for teaching one skilled in the art to employ the present disclosure.

Overview of the Disclosure

In various embodiments, the present disclosure describes computer-implemented methods and related systems for automatically generating an objective indication of oil quality and remaining oil life, if any, based simultaneously on multiple preselected key oil properties.

Generating the objective indication is automatic at least in that the processor, executing the algorithm disclosed herein, upon determining property data required by the algorithm (e.g., TAN and KV data), generates the indication without human interaction. The steps of determining the property data can also be automatic, as described further herein below.

The referenced indication has been termed a global oil deterioration index (or GODI), herein. The term is used in a non-limiting sense and other terms can be used to describe the index.

The algorithm of the present technology operates to combine, into a single consideration, data for the multiple preselected key oil properties, resulting in a single objective index value indicating oil quality. In one embodiment, described further below, the data includes, for each preselected property, a present-time value ($P_t$), a reference value ($P_o$), a predetermined deterioration-limit value ($P_d$), and a weight ($w_i$). Example oil properties include physical oil properties, such as kinematic viscosity (KV), and chemical oil properties, such as total acid number (TAN), oxidation, and nitration. Structure and operation of the algorithm are described further below.

The index value is an objective indication of oil quality and remaining oil life. It results from operation of the present algorithm and can be used in various ways. Uses of the resulting index value include calibrating and/or validating an engine oil life system, such as the Engine Oil Life System (EOLS) of the General Motors Company (e.g., EOLS II). In a contemplated embodiment, the algorithm of the present disclosure is a part of such an engine oil life system.

The index value can also be used for maintenance of an individual vehicle, or systematically for a large group of vehicles—e.g., as part of regular fleet management. Another example use of the index value is in analyzing performance of vehicle hardware, such as an effect of certain hardware on oil quality, engine oil life, or overall engine health. A vehicle design team considering whether to incorporate a new part, such as a turbo charger, could, for instance, compare index values for the vehicle, having the new charger, to that of the same vehicle without the new charger. The tests can be performed in the field (e.g., real-world driving) and/or in a laboratory environment, such as using a dynamometer.

For efficiency and readability, the present disclosure focuses primarily on the systems and methods of the present technology as implemented with automobile engine oil. The technology of the present disclosure is not limited to use in connection with automotive engine oil, though. The technology can be used in connection with oil of any type of vehicle, such as aircraft and watercraft.

FIG. 1

Now turning to the figures, and more particularly to the first figure, FIG. 1 illustrates a schematic block diagram of a system 100 for implementing the present technology. The system 100 in some embodiments is implemented as a computer for use in analyzing oil of a vehicle, such as an automobile. The system 100 can be remote to the vehicle, be a part of the vehicle, or, in one contemplated embodiment, be the vehicle, itself.

As shown in FIG. 1, the system 100 includes a computing unit 102. For embodiments in which the system 100 is associated with (e.g., includes, is, or is part of a vehicle), the computing unit 102 could be associated with an onboard computer unit (OCU). Alternatively or in addition, the computing unit 102 can also be associated with an electronic control module (ECM), such as an ECM designed to monitor and/or control use of engine oil.

The computing unit 102 includes a memory, or computer-readable medium 104, such as volatile medium, non-volatile medium, removable medium, and non-removable medium. The term computer-readable media and variants thereof, as used in the specification and claims, refer to tangible, non-transitory, storage media.

In some embodiments, storage media includes volatile and/or non-volatile, removable, and/or non-removable media, such as, for example, random access memory (RAM), read-only memory (ROM), electrically erasable programmable read-only memory (EEPROM), solid state memory or other memory technology, CD ROM, DVD, BLU-RAY, or other optical disk storage, magnetic tape, magnetic disk storage or other magnetic storage devices.

The computing unit 102 also includes a computer processor 106 connected or connectable to the computer-readable medium 104 by way of a communication link 108, such as a computer bus.

The computer-readable medium 104 includes computer-executable instructions 110. The computer-executable instructions 110 are executable by the processor 106 to cause the processor, and thus the computing unit 102, to perform any one or combination of the functions described herein. These functions are described, in part, below in connection with FIG. 2.

The computer-executable instructions 110 can be arranged in one or more software modules. The modules can be referred to by the act or acts that they cause the processor 106 to perform. For instance, a module including instructions that, when executed by the processor 106, cause the processor to perform a step of determining particular data can be referred to as an determining module. Similarly, a module causing the processor to calculate or determine a global oil deterioration index value can be referred to as a calculating module, a calculation module, an index-determining module, or the like.

The term software module, or variants thereof, is used expansively herein to include routines, program modules, programs, components, data structures, algorithms, and the like. Software modules can be implemented on various system configurations, including servers, network systems, single-processor or multiprocessor systems, minicomputers, mainframe computers, personal computers, hand-held computing devices, mobile devices, microprocessor-based, programmable consumer electronics, combinations thereof, and the like.

The processor 106 is also connected or connectable to at least one interface 112 for facilitating communications between the computing unit 102 and extra-unit devices 114/116.

For embodiments in which the system 100 is remote to the vehicle, the remote device 116, with which the system 100 can communicate via the interface 112, can include the vehicle.

For embodiments in which the system 100 is associated with the vehicle, the interface 112 can connect the computing unit 102 to other vehicle components 114 and/or remote devices 116.

In various embodiments, whether the system 100 is a part of the vehicle, the device 116 can include, for instance, nodes remote to the system 110, such as another computer, a removable storage device (e.g., flash drive), a near-field wireless device, or remote device accessible by way of a long-range communications network (e.g., a cellular or satellite network).

For short-range wireless communications, the interface, instructions, and processor are configured to use one or more short-range communication protocols, such as WI-FI®, BLUETOOTH®, infrared, infrared data association (IRDA), near field communications (NFC), Dedicated Short-Range Communications (DSRC), the like, and improvements thereof (WI-FI is a registered trademark of WI-FI Alliance, of Austin, Tex., and BLUETOOTH is a registered trademark of Bluetooth SIG, Inc., of Bellevue, Wash.).

In a contemplated embodiment, whether the system 100 is a part of the vehicle, the external device 116 includes one or more devices of a remote monitoring system such as the OnStar® monitoring system of the General Motors Company. The OnStar® system provides numerous services including remote-diagnostics and in-vehicle safety and security.

Although shown as being a part of the computing unit 102, completely, the interface 112, or any aspect(s) thereof, is in some embodiments partially or completely a part of the computing unit 102. The interface 112, or any aspect(s) thereof, can be partially or completely external to and connected or connectable to the computing unit 102. For communicating with the external device(s) 116, the interface 112 includes one or both of a short-range transceiver and a long-range transceiver.

The device(s) 114/116, internal or external to the computing unit 102, can include any of various devices acting as inputs and/or outputs for the unit 102. For at least some embodiments in which the device 114 includes one or more vehicle components 112, the device 114 includes at least one sensor configured to sense at least one property or characteristic of engine oil in the vehicle. Sensors 114 used by the computing unit 102 may also be used by an engine oil life system, such as the above-referenced EOLS.

Such sensors 114 can include one or more of (i) a viscosity sensor (e.g., viscometer), for measuring a level of oil viscosity of the engine oil, (ii) an oxidation sensor for measuring a level of oxidation of the engine oil, (iii) a nitration sensor for measuring a level of nitration of the engine oil, and (iv) a TAN sensor for determining a total acid number for the oil, such as by titration—e.g., a potentiometric titration or color indicating titration sensor. Other sensors 114 that could be used by the computing unit 102 include (v) a water-contamination sensor for measuring an amount (e.g., percentage or units) of water dilution, or contamination, of the oil, (vi) an engine oil level sensor, (vii) a fuel-contamination sensor for measuring an amount of fuel (e.g., gasoline) dilution, or contamination, of the oil, (viii) an engine oil temperature sensor, and (ix) an electrochemical oil quality sensor, for measuring electrochemical characteristics of the engine oil.

In some embodiments the sensors 114 also include those associated with measuring travel distance (e.g., mileage) of the vehicle. Such sensors include an odometer, or other devices for providing data related to an amount of vehicle travel, such as wheel sensors or parts of a global-positioning system.

Other example sensors 114 are those measuring engine conditions, such as real-time performance. In some embodiments, these sensors include those measuring engine combustion activity, such as a number of combustion events per unit time (e.g., per minute, hour, day, etc.).

In a contemplated embodiment, a single sensor performs two or more of the sensing functions described herein.

In some embodiments, the in-vehicle extra-unit devices 114 include a vehicle-user interface (VUI). The VUI facilitates user input to the vehicle and/or output from the vehicle to the user. An example VUI, is a visual display, such as a dashboard, overhead, or head-up display. The display could be a part of an instrument panel also including readouts for speed, engine temperature, etc. The display in some cases includes one or more light-emitting diodes (LEDs) or other lighting parts. Another example output device is a speaker for providing audible messages to the customer. The audible messages can be verbal (e.g., "An oil change is recommended") or non-verbal, such as a tone, beep, ring, buzz, or the like. The computing unit 102 is in some embodiments configured to provide both audible and visual communications to the customer, via an output device 114 such as substantially simultaneously in connection with the same event (e.g., upon determination that an oil change is needed).

As examples of input devices, or input aspect of an input/output device, the described display can include a touch-sensitive screen, and the vehicle can include a microphone, for receiving input from the user (e.g., instructions, settings or preference information, etc.).

Figure 2:
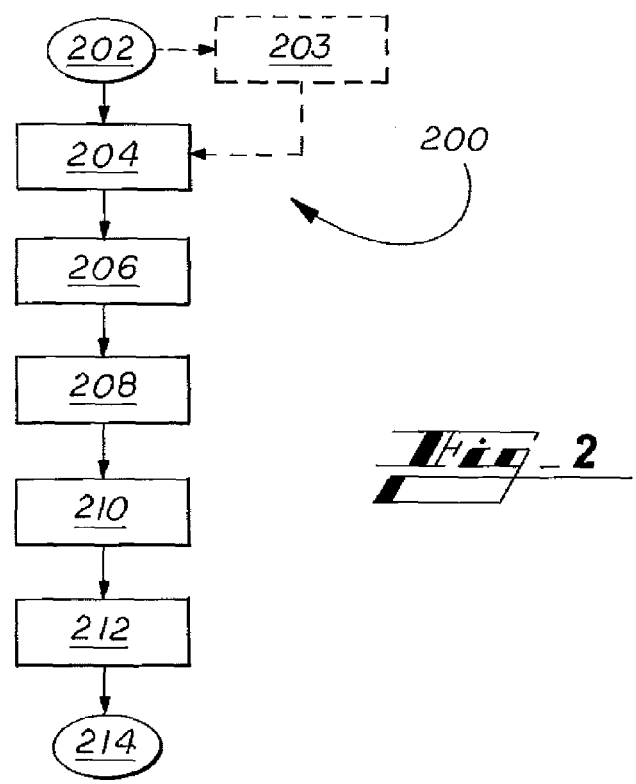
FIG. 2 illustrates a method for determining a global oil deterioration index, according to an embodiment of the present disclosure.
Figure 3:
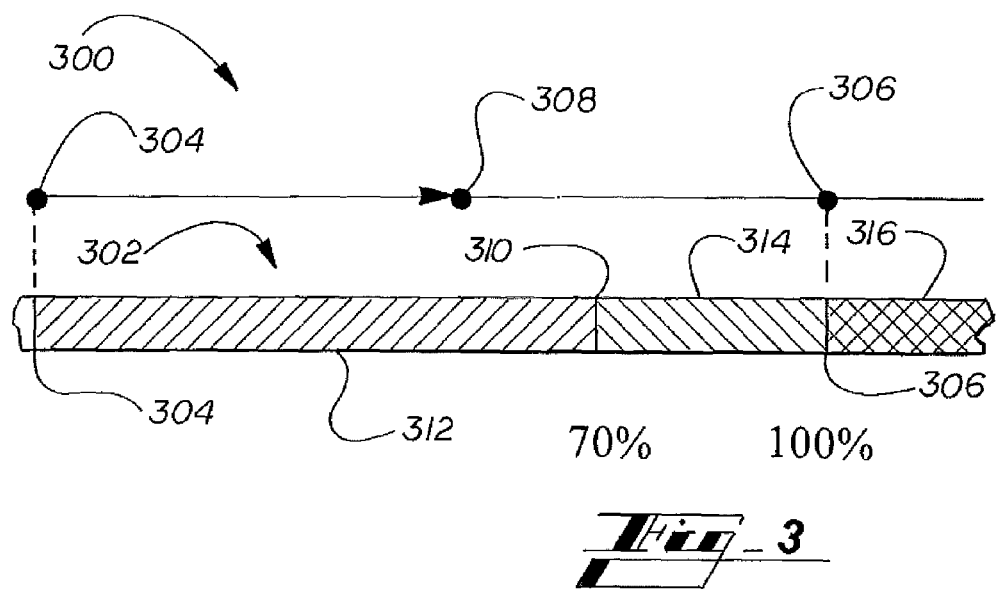
FIG. 3 illustrates schematically a concept of evaluating an oil property, according to an embodiment of the present disclosure.

FIGS. 2 and 3

FIG. 2 shows an exemplary method 200 for determining an objective indication of oil quality and remaining oil life, if any, based on multiple preselected key oil properties taken together. FIG. 3 shows a scale 300 to which variables of the method 200 can be compared.

The steps of the method 200 are not necessarily presented in any particular order and that performance of some or all the steps in an alternative order is possible and is contemplated. The steps have been presented in the demonstrated order for ease of description and illustration. Steps can be added, omitted and/or performed simultaneously without departing from the scope of the appended claims.

The illustrated method 200 can be ended at any time. In certain embodiments, some or all steps of this process, and/or substantially equivalent steps are performed by a processor, such as the processor 106, executing computer-readable instructions stored or included on a computer readable medium, such as the memory 104. In at least some of the embodiments in which the computing unit 102 is a part of a remote processing center, at least some of the instructions are part of a vehicle diagnostics system, such as an OnStar® Vehicle Diagnostics (OVD) system of General Motors®.

The method 200 begins 202 and flow proceeds to block 204 whereat a processor obtains or determines data indicative of a plurality of key properties of the engine oil used in a subject vehicle. The data can be input from a source remote to the computing device 102 and/or generated in the device itself. For embodiments in which the system 100 is a part of the vehicle, the data can also be received from another part of the vehicle, and/or from a source remote to the vehicle.

Notwithstanding the source, the data is at times referred to herein as input data, generally, and references to input data do not exclude embodiments in which the data is generated, and not received. Similarly, references herein, including in the claims, to determining such data is not limited to the data being generated, but determining the data (e.g., oil properties) includes embodiments in which the data is received from a source other than a presently-acting device (e.g. other than the processor of the system 100, or other than the system 100, itself).

The input data indicating oil properties can be referred to as oil-property data. The oil-property data is in some embodiments received from a device external to the processor performing the method. The external device can be, for instance, one or more of the external devices 114/116 described above in connection with FIG. 1.

The input data is in one embodiment received directly, such as via wired or wireless communication, or indirectly, such as via a flash drive or other removable storage device, from one or more oil-analysis instruments. The instrument(s) may be a part of a laboratory that is fully-automated or has lab personnel facilitating the analysis.

In some embodiments, the input data is received from an in-vehicle device 114, instead of or in addition to data received from an external source 116 (e.g., lab instrument(s)). As provided above, in-vehicle devices 114 can include sensors, such as (i) a viscosity sensor (e.g., viscometer), (ii) an oxidation sensor, (iii) a nitration sensor, and (iv) a TAN sensor (e.g., a potentiometric titration or color indicating the acidity of the oil).

The input data, from one or more of the devices 114/116, indicates engine oil properties such as viscosity, TAN, oxidation, and nitration. These exemplary properties are provided by way of example and the present technology is not limited to use of these four properties. For instance, the technology can be implemented with any combination of properties (a) including any one or more of these properties, (b) lacking any one or more of these properties, or (c) including one or more properties other than these properties. Regarding an exemplary property beyond the provided four that can be considered in the present method 200, the input data can indicate the quantity of pentane insoluble materials in the engine oil.

It should thus be appreciated that while processing of data indicating a certain number of oil properties (e.g., four or five properties) is discussed primarily herein, the technology presented can be implemented equally with any number of properties greater than one—e.g., a lower number of properties (e.g., two or three) or more properties (e.g., six, seven, . . . , n).

The particular properties for which input data is sought for use in the algorithm of the process 200 are carefully selected by a designer to ensure that the resulting index value is strongly indicative of the overall condition of the engine oil. The designer may decide not to use a certain property because the property changes generally in response to the same triggers that change one or more other properties being considered by the algorithm. In this example, the two properties would be redundant to an extent, and another property, more distinct from the one or other properties already selected for use in the algorithm would be preferred.

Although viscosity, e.g., kinematic viscosity, is generally the most commonly used oil property, it is described briefly here. Viscosity measurements are typically performed at a select test oil temperature. Viscosity can, only to a limited extent on its own, provide some indication of actual or potential corrosion problems and information about the amount of acids that have been formed.

Because viscosity is affected by the temperature of the oil, using a common temperature for tests of various oil samples allows for meaningful comparison between the samples. The various viscosities are usually identified with respect to the temperature of the oil. For instance, a measured value of kinematic viscosity made at 100° C. is commonly referred to as a KV100 value, one made at 40° C., KV40, etc. Kinematic viscosity of engine oil is typically measured in units of $mm^2/s$.

The total acid number (TAN) is another commonly-analyzed oil property. It can indicate, only to a limited extent on its own, actual or potential corrosion problems and provide information about the amount of acids that have been formed. Technically, the TAN is a number of milligrams of potassium hydroxide needed to neutralize acids in one gram of the engine oil. TAN values can be deduced by one or more processes, including those identified above.

Oxidation relates to the degree of oxidation of the oil. Oxidation is a summarizing parameter to characterize the amount of oxidation products in the oil. It can act as an early indicator for upcoming engine oil viscosity increase. It can be expressed as infrared absorbance per oil film thickness.

Nitration characterizes the nitration products in the oil that are early indicators prior to sludge formation. It can be expressed as infrared absorbance per oil film thickness.

Oxidation and Nitration also can, individually, and to limited extents alone, indicate actual or potential corrosion problems and provide information about the amount of acids that have been formed.

In some embodiments, the determining act 204 of FIG. 2 includes receiving input initiated by a user of the vehicle, a technician (e.g., user or auto shop technician), or another person who may be providing maintenance to the vehicle, designing the vehicle, testing a part on the vehicle, or testing an oil. Regarding testing a part, as provided above by way of example, a vehicle design team considering whether to incorporate a new part, such as a turbo charger, could, for instance, compare index values for the vehicle with the new charger to that of the vehicle having another charger or no charger. The tests can be performed in the field (e.g., real-world driving) and/or in a laboratory environment, such as using a dynamometer. The tests could also be performed to compare other factors, such as various types of oil—e.g., various brands and/or classifications (e.g., SAE viscosity grade classification)—in the same vehicle, the same type of oil in different types of vehicles, or different types of oils in different vehicles.

The determining act 204 can be performed regularly or intermittently, as part of repeat performances of the method 200 of FIG. 2. In one embodiment, the act 204 is performed at the vehicle generally continuously, such as at regular intervals with increments between performances, such as a day, week, or month, or at the vehicle or outside of the vehicle at longer intervals between.

In one embodiment, the obtaining act 204 is performed in response to a query or instruction (referred to as a query herein for simplicity), such as a query for oil quality, generally, or for more specific information, such as for the current GODI reading or remaining oil life information. The query can be generated locally, at the computing unit 102, received from a user (via a touch-screen or other VUI, e.g.), technician, other person, another part of the vehicle (e.g., EOLS II of General Motors®, or a remote device 116, such as the OnStar® monitoring system.

In some embodiments, the query is generated, at the vehicle or outside of the vehicle, in response to a determination that a triggering event has occurred. This optional determination act is identified by reference numeral 203 in FIG. 2. Example triggering events include a certain time having passed since the oil has been changed on a vehicle, the vehicle having traveled a certain distance since the oil has been changed on a vehicle, and an oil level reaching a preselected value (e.g., one liter low). Another example triggering event is a predetermined readout from a vehicle component, such as an oxidation readout for the oil of a predetermined value, a nitration readout of a predetermined value, a predetermined TAN value, or a predetermined kinematic viscosity value.

In one embodiment, at least some oil properties are represented on respective scales extending, for each property (e.g., KV, TAN, etc.), between an initial reference value ($P_o$), on the low end, up to a predetermined deterioration-limit value ($P_d$), which can also be referred to simply as a limit value. The limit value is determined as the point at which the particular property is considered to be in an undesirable range with respect to engine oil quality.

In various embodiments, the computer-readable instructions have data indicating these values for each of multiple oil properties (($P_o$), ($P_d$)) and/or the processor receives such data from a source external to the computing unit 102, such as from the devices 114/116. In some embodiments the instructions further include data indicating at least one intermediate warning level for the property P. The warning level could be, for instance, 70% or 75% of the value of $P_d$.

FIG. 3 illustrates some of these concepts schematically, for any given property P. The visual 300 includes a value scale 302 defined at least in part by a reference value ($P_o$), indicated by numeral 304, on or toward a low end of the scale 302. The value scale 302 is also defined by a predetermined deterioration-limit value ($P_d$) 306.

The visual 300 also identifies a present-time value ($P_t$) 308 for the property. The present value ($P_t$) 308 is the current value of the particular oil property (e.g., KV or TAN). The position of the present value ($P_t$) 308 on the scale 302 is shown by way of example in accord with a hypothetical scenario in which the present value ($P_t$) 308 is slightly over about 50%, or 0.5, of the values between the determined or predetermined deterioration-limit value ($P_d$) 306 and the determined or predetermined initial reference value ($P_o$). An intermediate warning level 310 is shown on the scale 302 at 70%, or 0.7, of $P_d$—i.e., 70% or 0.7 of the values between ($P_o$) 304 and ($P_d$) 306.

With continued reference to FIG. 3, the data indicating the reference value ($P_o$) 304, the predetermined deterioration-limit value ($P_d$) 306, and the intermediate warning level 310, define, in the instructions, a healthy, good, or safe zone 312, a buffer, or low or first-warning, zone 314, and a high or second-warning zone 316. In the visual 300, the safe zone 312 is indicated by hatch lines rising to the right, the low-warning zone 314 is indicated by hatch lines rising to the left, and the high-warning zone 316 is indicated by crossing hatch lines. In renditions of the same scale 302, these zones can be identified, e.g., as green, yellow, and red, respectively.

With reference to FIG. 3 and FIG. 2, then, the query (or instruction) causing the processor to perform the determining act 204 is, in one embodiment, initiated in response to a determination that at least one oil parameter $P_t$ has reached or surpassed the intermediate, or first-warning, level 310—i.e., the oil parameter $P_t$ has moved from the safe zone 312 to the low or first-warning zone 314. In another embodiment, the query (or instruction) causing the processor to perform the determining act 204 is initiated in response to a determination that the instant oil parameter $P_t$ has reached or surpassed the high, or second, warning, level 306—i.e., the oil parameter $P_t$ has moved from the first-warning zone 312 to the high or second-warning zone 316.

The algorithm of the present technology does not reach a final conclusion about overall engine oil quality based on the value P for a single parameter of the oil (e.g., kinematic viscosity or TAN) because, as indicated above, oil deteriorates in many distinct ways, and an oil sample might still be satisfactory overall though the single parameter is in a negative range, or unsatisfactory though a single parameter is in a positive range. In the given examples, an oil sample can be satisfactory overall for continued use though having an undesirably high TAN, and a sample can be unsatisfactory overall for continued use though having a healthy viscosity. For this reason, the present technology novelly generates an objective indication of oil quality and remaining oil life, if any, based on multiple preselected key oil properties taken together.

From the act 204 of determining the input data indicating the plurality of oil properties, flow of the algorithm proceeds to block 206 whereat the processor, executing the computer-readable instructions, performs an indexing routine on multiple preselected key engine oil properties. An instant (or current, or present) value $P_t$ has been obtained (e.g., received or generated at the computing unit 102), in one or more iterations of the determining act 204, for at least each of the multiple preselected key engine oil properties. The indexing routine need not process all data received at the computing unit 102, because instant values can be received for properties (e.g., oil volume or level) other than those processed in the indexing routine.

The indexing routine is configured, generally, to combine the instant values, for all of the multiple preselected key engine oil properties, determined (e.g., received or generated) in the determining act 204, into a single objective indication of oil health, or index value. The resulting index value, can be referred to as global because the index, and method for determining it (method 200, and particularly the present processing act 206) are useful across any desired group (or global selection), such as (I) a certain group of engine oils of a specification (e.g., the Dexos™ oil formulations of General Motors®), (II) a group of the same vehicles using a different oil, (III) a group of different vehicles using the same oil, (IV) etc. As provided, the term global oil deterioration index (GODI) has been coined. GODI is, though, used herein in a non-limiting sense, and other terms can be used equally in connection with the present technology, including in the present claims hereof, to describe the index value.

The indexing routine 206 combines the instant values, for the multiple preselected key engine oil properties, into a single objective indication, in any of numerous ways without departing from the scope of the present invention. In some embodiments, it is preferred that the instructions include, and/or the processor receives, at least one weighting factor (or weighting, or, simply, weight) specific to each oil property (e.g., KV, TAN, etc.) for processing in the routine 206. The weighting factor, which may be referenced generally as $w_i$, for each particular engine-oil property controls, a weight accorded to the particular property in a sub-operation of the routine. If it has been determined that the KV100 property is more important than the other preselected key engine-oil properties processed in the indexing routine, the weighting factor for the KV100 property could be set by a designer of the algorithm to have a relatively higher value than the weighting factors of the other key properties.

In one particular embodiment, described more below, a designer of the algorithm programs it so that all of the weighting factors, for the multiple preselected key oil properties, when added together, total one (1), and each particular weighting factor represents a calculated portion of the total based on the respective determined importance, or weight. For instance, following the example provided just above, wherein it has been determined that the KV100 property is more important than the other preselected key engine-oil properties processed in the indexing routine, the weighting factor for the KV100 property ($w_{KV100}$) could be set at 0.3, the TAN property ($w_{TAN}$) could be set at 0.25, the Oxidation property ($w_{Ox}$) could be set at 0.2, and the Nitration property ($w_{Nit}$) could be set at 0.25, for a sum of 1.0.

As described more below, the indexing routine of some embodiments also includes the reference or naught property value ($P_o$) (e.g., reference numeral 304 in FIG. 3) and the predetermined deterioration-limit value ($P_d$) (e.g., numeral 306). Values for these variables ($P_o$, $P_d$, $w_i$), or functions for use in determining their values, are predetermined by the designer. The values and functions can be predetermined in any of a variety of ways including by field tests, lab tests, calculations (e.g., interpolating or extrapolating from existing data).

In one embodiment, the instructions are configured such that the processor, in performing the indexing routine 206, performs the following summation to determine an index value (e.g., global oil deterioration index (GODI) value) [Eq. 1]:

$$GODI = \frac{1}{\sum_i w_i} \left( \sum_i \sqrt{\left[\frac{(P_{ti} - P_{0i})}{(P_{di} - P_{0i})}\right]^2 (w_i)} \right) \qquad \text{Eq. 1}$$

This equation [Eq. 1] includes $P_o$ as the reference value, $P_d$ as the deterioration-limit value, $P_t$ as the present-time value, and $w_i$ as the weighting factor.

In another embodiment, the instructions are configured such that the processor in performing the indexing routine 206, performs the following summation [Eq. 2]:

$$GODI = \frac{1}{\sum_i w_i} \left( \sum_i \left[\frac{(P_{ti} - P_{0i})}{(P_{di} - P_{0i})}\right]^2 (w_i) \right) \qquad \text{Eq. 2}$$

In still another embodiment, the instructions are configured such that the processor, in performing the indexing routine 206, performs one equation under certain predefined circumstances, such as based on one or more property values, such as a value of one or more of them falling within a preset range, or a certain relationship between two or more property values.

As a first example of the latter scenario (wherein which equation to perform depends on a relationship between two or more property values), the algorithm is configured to perform the first equation [Eq. 1] if the instant property value $P_t$ is greater than the corresponding deterioration-limit value $P_d$ for every key engine oil property being processed in the indexing routine 206 (e.g., for each of KV, TAN, Oxidation, and Nitration), and to perform the second equation [Eq. 2] otherwise (i.e., if any instant property value $P_t$ for the key properties is less than its corresponding deterioration-limit value $P_d$).

A designer of the algorithm can program the code to accommodate the case where $P_t = P_d$ for any of the key properties. For instance, the algorithm can configured to perform the second equation [eq. 2] if any instant property value $P_t$ for the properties is less than or equal to its corresponding deterioration-limit value $P_d$. Equations of this first particular embodiment can be represented as the following equation pair, [Eq. 3], [Eq. 4]:

$$GODI(\text{all } P_t < P_d) = \frac{1}{\sum_i w_i}\left(\sum_i \sqrt{\left[\frac{(P_{ti} - P_{0i})}{(P_{di} - P_{0i})}\right]^2 (w_i)}\right) \quad \text{Eq. 3}$$

$$GODI(\text{any } P_t \geq P_d) = \frac{1}{\sum_i w_i}\left(\sum_i \left[\frac{(P_{ti} - P_{0i})}{(P_{di} - P_{0i})}\right]^2 (w_i)\right) \quad \text{Eq. 4}$$

While Eq. 4 shows a greater-than-or-equal-to symbol between $P_t$ and $P_d$, in one embodiment this symbol, in the same location of the equation (Eq. 4), is, instead, a greater-than sign; Correspondingly, Eq. 3 would have a less-than-or-equal-to symbol $P_t$ and $P_d$ between instead of a less-than symbol shown above for Eq. 3.

As a second example of the scenario (wherein which equation to perform depends on a relation between two or more property values), in another particular embodiment, the algorithm is configured to perform the second equation [Eq. 2] if the instant property value $P_t$ is less than the corresponding deterioration-limit value $P_d$ for every property (e.g., for KV, TAN, Oxidation, and Nitration), and to perform the first equation [eq. 1] otherwise (i.e., if any instant property value $P_t$ for the properties is greater than (or greater than or equal to) its corresponding deterioration-limit value $P_d$).

Equations in this second particular embodiment can be represented as the following equation pair, [Eq. 5], [Eq. 6]:

$$GODI(\text{any } P_t \leq P_d) = \frac{1}{\sum_i w_i}\left(\sum_i \sqrt{\left[\frac{(P_{ti} - P_{0i})}{(P_{di} - P_{0i})}\right]^2 (w_i)}\right) \quad \text{Eq. 5}$$

$$GODI(\text{all } P_t > P_d) = \frac{1}{\sum_i w_i}\left(\sum_i \left[\frac{(P_{ti} - P_{0i})}{(P_{di} - P_{0i})}\right]^2 (w_i)\right) \quad \text{Eq. 6}$$

While Eq. 5 shows a less-than-or-equal-to symbol between $P_t$ and $P_d$, in one embodiment this symbol, in the same place in the equation (Eq. 5), is, instead, a less-than symbol; Eq. 6 would correspondingly have a greater-than-or-equal-to symbol, between $P_t$ and $P_d$, instead of the greater-than symbol shown above for Eq. 6.

For any of the above-referenced index routines, $w_i$ can be set as indicated above, and as follows [Eq. 7]:

$$\sum_i w_i = 1 \quad \text{Eq. 7}$$

In this way, as provided above, the weighting factors for all of the preselected key oil properties, when added together, total one (1), each representing a predetermined portion of the total according to the importance accorded to each property by the designer of the algorithm.

As provided, the predetermined weightings ($w_i$) are also set, as desired, by a designer of the algorithm, such as based on present and/or historic lab and/or field tests. In one exemplary embodiment, the algorithm is programmed to determine one, all, or any combination of the following values for the deterioration limit ($w_i$):

|  | $w_i$ |
|---|---|
| KV100 | 2 |
| TAN | 1 |
| Oxidation | 1 |
| Nitration | 1 |

According the values of this chart to embodiments in which the summation of weightings $w_i$ is one (1), as mentioned above, the particular $w_i$ values would equate to the weighting for the KV100 property ($w_{KV100}$) being set at 0.4 and the weightings for each of the other properties (e.g., ($w_{TAN}$), ($w_{Ox}$), ($w_{Nit}$)) being set at 0.2.

In some embodiments, the preference property value $P_0$ is, for each key engine-oil property being processed according to any of the above-referenced index routines (e.g., Eq. 1, Eq. 2, the Eq. 3/4 function pair, and the Eq. 5/6 function pair), a value for the property that new or unused oil would have. For scenarios in which the reference property value is not determinable based on the oil type [e.g., because the oil type is unknown or information for the value based on the oil type is unavailable, or the algorithm is otherwise configured to resort to a default value (e.g., to achieve a savings of processing resources and/or processing time)], the algorithm can use a predetermined default value for the preference property value $P_0$ for that property.

In some embodiments, such default value(s) can be dependent, depending on one or more other characteristics or circumstances, such as a type or brand of oil being used, a type of vehicle or engine, a total mileage or other indication of age, use, or wear on the vehicle, and the like. Regarding example default values, in one embodiment, the algorithm is programmed to include one, all, or any combination of the following default values for reference property values ($P_o$):

|  | Default $P_0$ | Sub-variable |
|---|---|---|
| KV100 | 8.5 | SAExW-20 oil |
|  | 10 | SAExW-30 oil |
|  | 14 | SAExW-40 oil |
| TAN | 2 | — |
| Oxidation | (see right) | $P_0$ is the average of known new-oil Ox values for all, or some subset of, available engine oils |
| Nitration | (see right) | $P_0$ is the average of known new-oil Nit values for all, or some subset of, available engine oils |

As provided, the predetermined deterioration-limit values ($P_d$) are also set, as desired, by a designer of the algorithm, such as based on present and/or historic lab and/or field tests. In one embodiment, the algorithm is programmed to, for any of the above-referenced index routines (e.g., Eq. 1, Eq. 2, the Eq. 3/4 function pair, and the Eq. 5/6 function pair), determine any of the values as a preset value or according to a preset relationship, such as to the reference property ($P_o$). In one case, the algorithm may assign the following values for the deterioration limit ($P_d$):

|  | $P_d$ |
| --- | --- |
| KV100 | $1.5 \times P_o$ |
| TAN | 7 |
| Oxidation | $30 + P_o$ |
| Nitration | $40 + P_o$ |

As provided, in most embodiments of the present technology, it is preferred that the indexing act 206 of FIG. 2, result in a single indication or index value, e.g., a single GODI. In some embodiments, the method 200 includes an act 208 subsequent to the indexing act 206, of categorizing (or labeling, grouping, or the like) the resulting index value.

In one embodiment, the algorithm uses a scale similar in ways to the scale 302 of FIG. 3. As an example, the algorithm can be programmed so that the indexing routine causes the resulting index value to be above 1.0 if the oil is considered generally unsatisfactory for intended purposes, or at least close to being so if the value is at or quite close to 1.0 and more so if the value is relatively high above 1.0 relatively.

As with the values for the constituent property values (P), as described above in connection with FIG. 3, the values for the resulting index value can be represented as a percentage or point value. For instance, a 1.0 point value for the index can equate to 100% of a scale for the index, 0.5 equates to 50%, and so on.

In one contemplated embodiment, the algorithm can include further detailed differentiations such that, for instance, the processor categorizes (labels, etc.) the oil as satisfactory, but less so, for values below but closer to 1.0 (or 100%), and satisfactory, and more so, for value farther below 1.0, relatively. The further degradations can take any of various forms, such as a naming convention having two, three, four, or more different names corresponding to various values and/or ranges of index values. For instance, the algorithm may cause the processor to label the oil as superb or very healthy if the resulting index value is between 0.5 (or 50%) and 0.6 (or 60%), as good if between 0.6 and 0.7, satisfactory, poor, or low-warning-level, or oil-changed-needed-soon, if between 0.7 and 1.0, and poor, high-warning level, or change-needed-now, if above 1.0.

Similarly, as also referenced above in connection with the scale 302 of FIG. 3, categorizations can be indicated by colors, such as green, yellow, and red.

As indicated above, the entire method 200 or any acts therein, e.g., the indexing act 206, can be performed, or iterated, multiple times. For instance, the method, or just the indexing act 206 can be performed separate times for each of distinct scenarios, such as once for each of multiple types of oil being used in the same vehicle, or once for each of distinct vehicles (e.g., different brands or types of vehicle, or the same vehicle having one or more different parts per scenario)

As referenced above, an output of the present method 200 can be an indication of the remaining life of the oil. In most embodiments, the index value resulting from the indexing act 206 itself (e.g., GODI) provides this indication of remaining oil life, whereby an evaluator (person or specially-programmed computing device) recognizes that lower index values equate to more life and higher index values equate to less.

In at least one embodiment, the algorithm of the present technology is configured such that the GODI begins at about 0.0, for fresh oil, and increases as the oil degrades. In a particular embodiment, a healthy life span of an engine oil is generally considered to extend from a GODI range of about 0.0 to about 0.5. The actual effective life span of any specific oil in a specific vehicle may vary, though, such that oil having a GODI of greater than 0.5, or even 0.7, in some cases, may still provide effective engine protection.

In some embodiments of the present technology, the algorithm is configured to determine an indication of oil life, such as remaining life, according to a preset relationship between index values (e.g., GODIs) and life indications. In one particular embodiment, presented merely as a general example, the algorithm is configured so that, assuming a maximum drain of 8,000 miles or about 15 weeks (or equivalent, e.g., months, days, minutes, etc.), a GODI between 0.0 to 0.1 indicates that the oil has a remaining life of about 2,500 to 6,800 miles of driving, or in terms of time, about 12-15 weeks of operation, a GODI between 0.1 and 0.2 indicates that the oil has a remaining life of about 2,000 to 3,500 miles of driving, or in terms of time, perhaps 11-15 weeks of driving, and so on, e.g., to a GODI of 0.7 or more corresponding to 0 miles and 0 days of life remaining according to the programmed recommendation of the system.

In another exemplary embodiment, relating to jurisdictions using kilometers, such as Europe, the algorithm is configured so that, assuming a maximum drain of 30,000 km or 12 months (or equivalent, e.g., weeks, days, minutes, etc.), a GODI between 0.0 to 0.1 indicates that the oil has a remaining life of about 20,000 to about 25,700 km, or in terms of time, about 10-12 months of operation, a GODI between 0.1 and 0.2 indicates that the oil has a remaining life of about 15,000 to 23,000 km of driving, or in terms of time, perhaps 7-10 months of driving, and so on, e.g., to a GODI of 0.7 or more corresponding to 0 km and 0 days of life remaining according to the programmed recommendation of the system.

Continuing with the method 200 of FIG. 2, following determination of the index value (e.g., GODI) at act 206, and with, before, or after the classification act 208, if the classification act is performed, the algorithm includes an outputting act 210 whereat the processor, executing the computer-readable instructions, performs at least one output function using the index value.

In most embodiments, the processor in this outputting act 210 generates one or more communications having (i) the resulting index value, (ii) an indication of oil life, (iii) a signal representative of the index value or oil life, and/or (iv) a message based on the resulting index value and/or the determined oil life.

The outputting act 210 in some embodiments includes transmitting the communication(s) for receipt by an interested entity. The interested entity could be, for instance, an owner of the vehicle, a designer of the vehicle, a manufacturer of the vehicle, a technician working on the vehicle, a person responsible for the vehicle (e.g., manager of a fleet of which the vehicle is a part), and/or a computer or person of a customer service, such as the OnStar® service.

In some embodiments, acts performed after the outputting act 210, at and/or outside of the vehicle, are considered a part of the method, and are represented generally by reference numeral 212 in FIG. 2.

In some embodiments, (i) the resulting index value and/or (ii) the indication of oil life (e.g., estimated useful life remaining for the oil) are used, at act 212, by a receiving interested entity to determine whether an oil change is needed for the vehicle. The index value or indication of oil life could be communicated via signal or message. For example, the value or indication can be communicated to a person in the vehicle (e.g., owner, driver, or technician) as a signal or message via a display screen, speaker, or indicator light of the vehicle.

A message can be communicated to a receiving interested entity in any of a variety of ways, including by e-mail, short-messaging system (SMS) message, multimedia-messaging system (MMS) message, voice message, facsimile, paper, and/or other.

In some embodiments, at act 212, the resulting index value or oil life data, is used by a receiving interested entity to calibrate and/or validate a system such as an engine oil life system (e.g., the EOLS system of General Motors®). The calibrating or validating can include setting, or confirming the accuracy of, limits of the EOLS. Generally, an engine oil life system monitors various vehicle operating conditions, such as speed, mileage, engine temperature, time since last oil change, oil level, driving habits, climate, and recommends when vehicle engine oil should be changed. Goals of the system include saving the driver money and time and reducing waste oil, such as by avoiding oil changes before a change is recommended, and increasing vehicle engine life, such as by ensuring an oil change is not made after, or not made long after, a recommended time.

In some embodiments, at act 212, the resulting index value or oil life data is used, as also referenced above, in the maintenance of an individual vehicle or systematically for a large group of vehicles as part of fleet management. An entity associated with fleet management can have associated fleet-management software for processing information received from the processor 102, for initiating and facilitating decision making by a manager concerning the vehicles in the fleet.

In some embodiments, at act 212, the resulting index value or indication of oil life is used in analyzing the effect of various vehicle hardware changes on the vehicle. For instance, a designer, or vehicle design team, considering whether to incorporate a new part, such as a turbo charger, could compare an index value for the oil after used in the vehicle with the new charger to the index value for the same oil for the same vehicle without the new charger.

From block 212, flow of the algorithm can end at 214 or proceed to the beginning 202 of the method 200 whereby the method 200 is performed again.

FIG. 4

Figure 4:
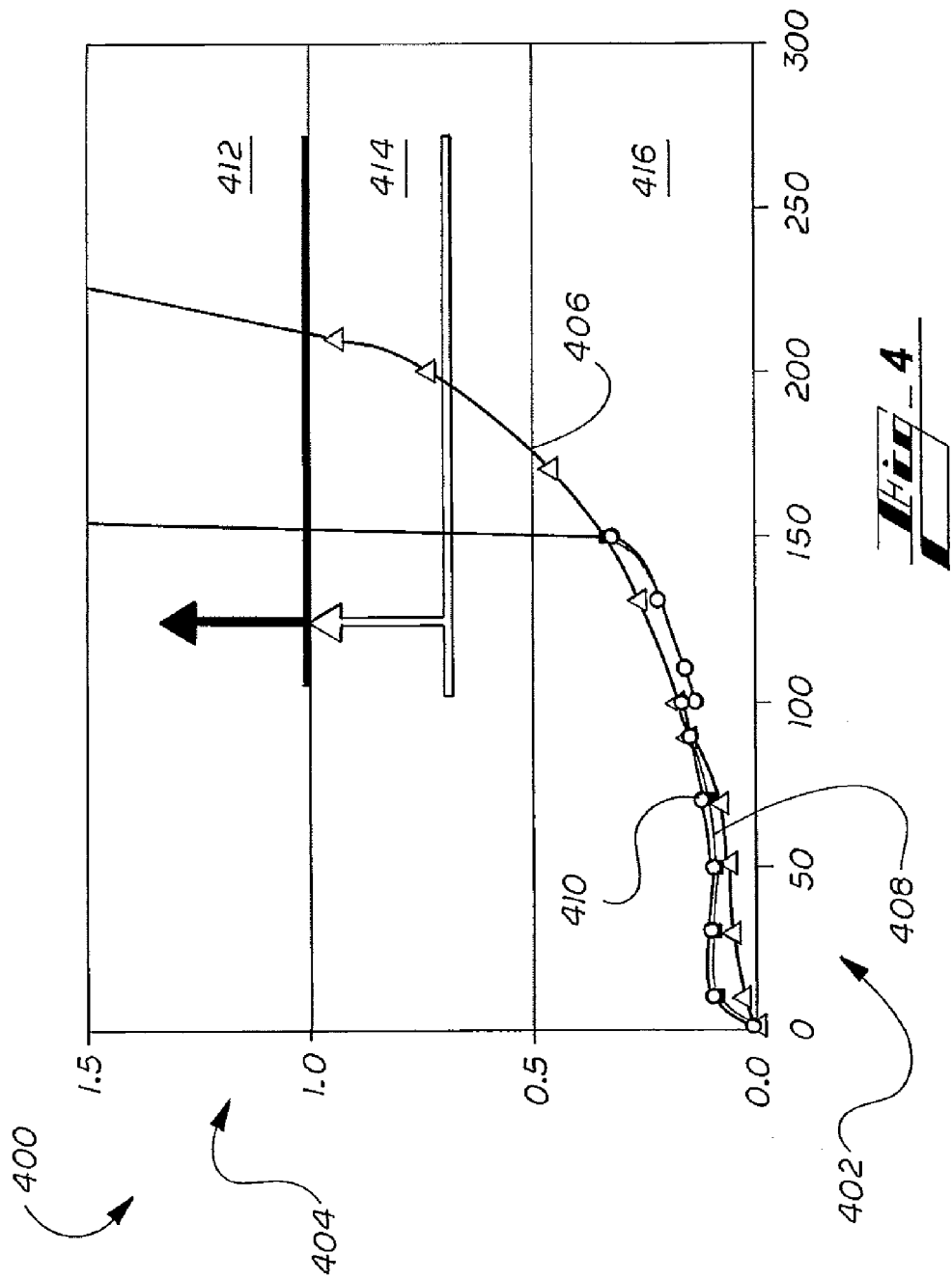
FIG. 4 is a graph showing values for global oil deterioration index with time for example tests of different engine oils.

FIG. 4 illustrates a chart 400 showing results of exemplary tests performed in accord with the present technology. An x-axis 402 represents engine operating features, such as engine operating time, engine revolutions, etc. The particular feature depicted is engine operating time as measured in hours and, as shown, the x-axis is demarcated between 0 and 300 hours. The y-axis 404 represents an index value, such as a global oil deterioration index (GODI). As shown, the y-axis 404 can range from 0.0 to 1.5.

The chart 400 shows index values (e.g., GODI), over time, for a first oil, indicated by reference numeral 406. The chart also shows index values 408 from a first test, for a second oil, and index values 410 from a second test for the same second oil. The chart 400 also shows three zones, corresponding to those described above, including a first, high-warning zone, indicated by reference numeral 412 (e.g., a red zone), a second, low-warning zone 414 (e.g., yellow), and a third, safe, zone 416 (e.g., green zone).

CONCLUSION

Various embodiments of the present disclosure are disclosed herein. The disclosed embodiments are merely examples that may be embodied in various and alternative forms, and combinations thereof. For instance, methods performed by the present technology are not limited to the aspects described above in connection with the method 200 illustrated schematically in FIG. 2.

The law does not require and it is economically prohibitive to illustrate and teach every possible embodiment of the present claims. Hence, the above-described embodiments are merely exemplary illustrations of implementations set forth for a clear understanding of the principles of the disclosure. Variations, modifications, and combinations may be made to the above-described embodiments without departing from the scope of the claims. All such variations, modifications, and combinations are included herein by the scope of this disclosure and the following claims.

What is claimed is:

1. A system, comprising:

a plurality of sensor devices comprising a first sensor device and a second sensor device sensing distinct properties of oil used in a vehicle and generating first sensor-device data and second sensor-device data respectively; and a processing device configured to receive the first sensor-device data from the first sensor device and determine, regarding a first oil property of the distinct properties for the oil used in the vehicle, a first set of oil-property characteristics comprising:

a first presently-measured oil-property value ($P_{t1}$) based on the first sensor-device data;

a first reference-oil-property value ($P_{o1}$);

a first deterioration-limit value ($P_{d1}$); and a first weighting factor ($w_1$) representing a first pre-determined level of importance assigned to the first oil property;

wherein the processing device is further configured to receive the second sensor-device data from the second sensor device and determine, regarding a second oil property of the distinct properties for the oil used in the vehicle, a second set of oil-property characteristics, comprising:

a second presently-measured oil-property value ($P_{t2}$) based on the second sensor-device data;

a second reference-oil-property value ($P_{o2}$);

a second deterioration-limit value ($P_{d2}$); and a second weighting factor ($w_2$) representing a second pre-determined level of importance assigned to the second oil property; and wherein the processing device is further configured to generate, using at least the first set of oil-property characteristics and the second set of oil-property characteristics, a system output comprising a single index value indicating a state of deterioration of the oil used by the vehicle, and the generating including performing at least one of a first function and a second function for determining an oil-deterioration index (ODI) as the single index value, the first and second functions being, respectively, as follows:

$$ODI = \frac{1}{\sum_i w_i}\left(\sum_i \sqrt{\left[\frac{(P_{ti} - P_{0i})}{(P_{di} - P_{0i})}\right]^2 (w_i)}\right); \text{ and}$$

$$ODI = \frac{1}{\sum_i w_i}\left(\sum_i \left[\frac{(P_{ti} - P_{0i})}{(P_{di} - P_{0i})}\right]^2 (w_i)\right).$$

2. The system of claim 1, wherein:
the processing device, in being configured to generate the system output, is configured to perform the first function if, for each of the distinct properties of oil, the determined presently-measured oil property is less than the determined deterioration-limit value, and perform the second function otherwise;
the first function is represented then by:

$$ODI(\text{all } P_t < P_d) = \frac{1}{\sum_i w_i}\left(\sum_i \sqrt{\left[\frac{(P_{ti} - P_{0i})}{(P_{di} - P_{0i})}\right]^2 (w_i)}\right);$$

the second function is represented then by:

$$ODI(\text{any } P_t \geq P_d) = \frac{1}{\sum_i w_i}\left(\sum_i \left[\frac{(P_{ti} - P_{0i})}{(P_{di} - P_{0i})}\right]^2 (w_i)\right).$$

3. The system of claim 1, wherein:
the processing device, in being configured to generate the system output, is configured to perform the first function if, for any of the distinct properties of oil, the determined presently-measured oil property is less than or equal to the determined deterioration-limit value, and perform a second function otherwise;
the first function is represented then by:

$$ODI(\text{any } P_t \leq P_d) = \frac{1}{\sum_i w_i}\left(\sum_i \sqrt{\left[\frac{(P_{ti} - P_{0i})}{(P_{di} - P_{0i})}\right]^2 (w_i)}\right);$$

the second function is represented then by:

$$ODI(\text{all } P_t > P_d) = \frac{1}{\sum_i w_i}\left(\sum_i \left[\frac{(P_{ti} - P_{0i})}{(P_{di} - P_{0i})}\right]^2 (w_i)\right).$$

4. The system of claim 1, wherein:
the processing device is further configured to determine, regarding a third oil property of said distinct properties of oil, a third set of oil-property characteristics comprising:
a third presently-measured oil-property value ($P_{t3}$);
a third reference-oil-property value ($P_{o3}$);
a third deterioration-limit value ($P_{d3}$); and
a third weighting factor ($w_3$) representing a third predetermined level of importance assigned to the third oil property; and
the processing device, in being configured to generate the system output, is configured to generate the system output using at least the first, second, and third sets of oil-property characteristics.

5. The system of claim 4, wherein:
the processing device is further configured to determine, regarding a fourth oil property of said distinct properties of oil, a fourth set of oil-property characteristics comprising:
a fourth presently-measured oil-property value ($P_{t4}$);
a fourth reference-oil-property value ($P_{o4}$);
a fourth deterioration-limit value ($P_{d4}$); and
a fourth weighting factor ($w_4$) representing a third predetermined level of importance assigned to the third oil property; and
the processing device, in being configured to generate the system output, is configured to generate the system output using at least the first, second, third, and fourth sets of oil-property characteristics.

6. The system of claim 1, wherein the first oil property and the second oil property are distinct oil properties selected from a group consisting of:
kinematic viscosity (KV);
total acid number (TAN);
oxidation; and
nitration.

7. The system of claim 1, wherein the processing device, in being configured to determine the first values and the first weighting factor, is configured to obtain at least one of the first reference-oil-property value ($P_{o1}$), the first deterioration-limit value ($P_{d1}$), and the first weighting factor ($w_1$) from a source remote to the system.

8. The system of claim 1, wherein:
the oil was used in a vehicle; and
the processing device, in being configured to determine the first presently-measured oil-property value ($P_{t1}$), is configured to receive an indication of the first presently-measured oil-property value ($P_{t1}$) from the first sensor device.

9. The system of claim 1, wherein the processing device is further configured to transmit, for receipt by an interested entity, a message or other signal in response to determining the single index value.

10. The system of claim 9, wherein the message or signal is configured to indicate the single index value.

11. The system of claim 1, wherein the processing device is further configured to determine an indication of remaining life for the engine oil using the single index value.

12. The system of claim 1, wherein the processing device is further configured to categorize the oil into one of multiple preset quality categories based on the single index value.

13. The system of claim 1, wherein an entirety of the system is part of the vehicle.

14. A method, performed by a system configured to generate, based on sensor data corresponding to a plurality of oil properties, a system output indicative of a state of deterioration of engine oil used by a vehicle, the method comprising:
obtaining, by way of a first sensor device, first sensor-device data regarding a first property for the oil used in the vehicle;
obtaining, by way of a second sensor device, second sensor-device data regarding a second property, distinct from the first property, for the oil used in the vehicle;
determining, by a processing device of the system, regarding the first oil property, a first set of oil-property characteristics, comprising:
a first presently-measured oil-property value ($P_{t1}$) based on the first sensor-device data;
a first reference-oil-property value ($P_{o1}$);
a first deterioration-limit value ($P_{d1}$); and a first weighting factor ($w_1$) representing a first predetermined level of importance assigned to the first oil property;
determining, by the processing device of the system, regarding the second oil property, a second set of oil-property characteristics, comprising:
a second presently-measured oil-property value ($P_{t2}$) based on the second sensor-device data;
a second reference-oil-property value ($P_{o2}$);
a second deterioration-limit value ($P_{d2}$); and
a second weighting factor ($w_2$) representing a second pre-determined level of importance assigned to the second oil property; and
generating, using at least the first set of oil-property characteristics and the second set of oil-property characteristics, the system output comprising a single index value indicating the state of deterioration of the engine oil, wherein the generating includes performing at least one of two functions for determining an oil-deterioration index (ODI) as the single index value, the functions being as follows:

$$ODI = \frac{1}{\sum_i w_i}\left(\sum_i \sqrt{\left[\frac{(P_{ti}-P_{0i})}{(P_{di}-P_{0i})}\right]^2 (w_i)}\right);$$

and $$ODI = \frac{1}{\sum_i w_i}\left(\sum_i \left[\frac{(P_{ti}-P_{0i})}{(P_{di}-P_{0i})}\right]^2 (w_i)\right).$$

15. The method of claim 14, wherein the first oil property and the second oil property are distinct properties selected from a group consisting of:
kinematic viscosity (KV);
total acid number (TAN);
oxidation; and
nitration.

16. The method of claim 14, wherein determining the first values and the first weighting factor comprises obtaining at least one of: the first reference-oil-property value ($P_{o1}$), the first deterioration-limit value ($P_{d1}$), and the first weighting factor ($w_1$) from a source remote to the system.

17. The method of claim 14, wherein the processing device is further configured to categorize the engine oil into one of multiple preset quality categories based on the single index value.

18. A non-transitory storage device configured for use with a system to generate, based on sensor data corresponding to a plurality of oil properties, a system output indicative of a state of deterioration of engine oil used by a vehicle, the non-transitory storage device comprising code, which, when executed by a processor of the system, causes the processor to perform functions comprising:
obtaining, by way of a first sensor device, first sensor-device data regarding a first property for the oil used in the vehicle;
obtaining, by way of a second sensor device, second sensor-device data regarding a second property, distinct from the first property, for the oil used in the vehicle;
determining, regarding the first oil property of said plurality of oil properties, a first set of oil-property characteristics, comprising:
a first presently-measured oil-property value ($P_{t1}$) based on the first sensor-device data;
a first reference-oil-property value ($P_{o1}$);
a first deterioration-limit value ($P_{d1}$); and
a first weighting factor ($w_1$) representing a first predetermined level of importance assigned to the first oil property;
determining, regarding the second oil property of said plurality of oil properties, a second set of oil-property characteristics, comprising:
a second presently-measured oil-property value ($P_{t2}$) based on the second sensor-device data;
a second reference-oil-property value ($P_{o2}$);
a second deterioration-limit value ($P_{d2}$); and
a second weighting factor ($w_2$) representing a second pre-determined level of importance assigned to the second oil property; and
generating, using at least the first set of oil-property characteristics and the second set of oil-property characteristics, the system output indicative comprising a single index value indicating the state of deterioration of the engine oil, wherein the generating comprises determining an oil-deterioration index (ODI) as the single index value according to at least one of two functions being as follows:

$$ODI = \frac{1}{\sum_i w_i}\left(\sum_i \sqrt{\left[\frac{(P_{ti}-P_{0i})}{(P_{di}-P_{0i})}\right]^2 (w_i)}\right);$$

and $$ODI = \frac{1}{\sum_i w_i}\left(\sum_i \left[\frac{(P_{ti}-P_{0i})}{(P_{di}-P_{0i})}\right]^2 (w_i)\right).$$

19. The non-transitory storage device of claim 18, wherein the first oil property and the second oil property are distinct oil properties selected from a group consisting of:
kinematic viscosity (KV);
total acid number (TAN);
oxidation; and
nitration.

20. The non-transitory storage device of claim 18, wherein the function of determining the first values and the first weighting factor comprises obtaining at least one of: the first reference-oil-property value ($P_{o1}$), the first deterioration-limit value ($P_{d1}$), and the first weighting factor ($w_1$) from a source remote to the system.

* * * * *